(12) United States Patent
Raschke et al.

(10) Patent No.: US 10,888,719 B2
(45) Date of Patent: Jan. 12, 2021

(54) ACTIVE SUBSTANCE COMBINATION OF CREATINE AND/OR CREATININE AND PHENOXYETHANOL

(75) Inventors: Thomas Raschke, Pinneberg (DE); Christopher Mummert, Bienenbüttel (DE); Volker Kallmayer, Hamburg (DE)

(73) Assignee: BEIERSDORF AG, Hamburg (DE)

( * ) Notice: Subject to any disclaimer, the term of this patent is extended or adjusted under 35 U.S.C. 154(b) by 297 days.

(21) Appl. No.: 10/995,200

(22) Filed: Nov. 24, 2004

(65) Prior Publication Data

US 2005/0137260 A1 Jun. 23, 2005

(30) Foreign Application Priority Data

Nov. 26, 2003 (DE) .................................. 103 55 714

(51) Int. Cl.
| | |
|---|---|
| *A61Q 19/00* | (2006.01) |
| *A61K 31/198* | (2006.01) |
| *A61K 8/39* | (2006.01) |
| *A61Q 17/00* | (2006.01) |
| *A61Q 19/08* | (2006.01) |
| *A61K 8/44* | (2006.01) |

(52) U.S. Cl.
CPC .............. *A61Q 19/00* (2013.01); *A61K 8/39* (2013.01); *A61K 8/44* (2013.01); *A61K 31/198* (2013.01); *A61Q 17/00* (2013.01); *A61Q 19/08* (2013.01); *A61K 2800/59* (2013.01)

(58) Field of Classification Search
CPC ....................................................... A61K 8/44
See application file for complete search history.

(56) References Cited

U.S. PATENT DOCUMENTS

| | | | |
|---|---|---|---|
| 4,144,325 A | 3/1979 | Voyt | |
| 4,248,861 A | 2/1981 | Schutt | |
| 4,590,067 A | 5/1986 | Meisner | |
| 4,647,453 A | 3/1987 | Meisner | |
| 5,091,171 A | 2/1992 | Yu et al. | |
| 5,422,112 A | 6/1995 | Williams | |
| 5,834,513 A | 11/1998 | Ptchelintsev et al. | |
| 5,939,078 A | 8/1999 | Fujimura et al. | |
| 6,242,491 B1* | 6/2001 | Kaddurah-Daouk | 514/565 |
| 6,355,752 B1 | 3/2002 | Brungs et al. | |
| 6,372,234 B1* | 4/2002 | Deckers | A23D 7/001 424/400 |
| 6,413,552 B1* | 7/2002 | Stoll | 424/728 |
| 6,432,424 B1 | 8/2002 | Shapiro et al. | |
| 7,150,880 B2* | 12/2006 | Howard et al. | 424/439 |
| 2002/0048603 A1 | 4/2002 | Burmeister et al. | |
| 2004/0018162 A1 | 1/2004 | Bimczok et al. | |
| 2004/0029969 A1* | 2/2004 | Blatt et al. | 514/565 |
| 2004/0247541 A1 | 12/2004 | Wendel et al. | |
| 2004/0258717 A1 | 12/2004 | Sauermann et al. | |

FOREIGN PATENT DOCUMENTS

| | | | |
|---|---|---|---|
| DE | 10032964 | 1/2002 | |
| EP | 0178602 | 4/1986 | |
| EP | 0565010 | 10/1993 | |
| FR | 2725896 | 4/1996 | |
| FR | 2734721 | 12/1996 | |
| GB | 2357970 A | 7/2001 | |
| JP | 9-202709 | 8/1997 | |
| JP | 9-202710 | 8/1997 | |
| JP | 9-263511 | 10/1997 | |
| JP | 2000-247866 | 9/2000 | |
| JP | 2000247866 A * | 9/2000 | ............... A61K 7/48 |
| WO | 0015187 A1 | 3/2000 | |
| WO | 00/33787 | 6/2000 | |
| WO | 02/02075 | 1/2002 | |
| WO | 02/076408 | 10/2002 | |
| WO | 2003011241 A1 | 2/2003 | |
| WO | 2003020235 A | 3/2003 | |

OTHER PUBLICATIONS

English Language Abstract of JP 2000-247866.
A. Deflandre and G. Lang, International Journal of Cosmetic Science, 10, 53-62 (1988).
A. Voelckel et al., Zentralblatt Haut- und Geschlechtskrankheiten, 156, 1-15 (1989).
Y. Miyachi "Skin Diseases Associated with Oxidative Injury" in "Oxidative Stress in Dermatology", edited by J. Fuchs and L. Packer, Marcel Dekker, Inc., New York, Basel, Hong Kong, 1993, pp. 323-331.
U.S. Appl. No. 10/995,208, filed concurrently with the present application and entitled "Active Substance Combination of Creatine and/or Creatinine and Organic Thickeners".
U.S. Appl. No. 10/995,203, filed concurrently with the present application and entitled "Active Susbstance Combination of Creatine and/or Creatinine and a Retinoid".
English Language Abstract of JP 9-202709.
English Language Abstract of JP 9-202710.
English Language Abstract of JP 9-263511.
English Language Abstract of FR 2725896.
English Language Abstract of FR 2734721.
Database GNPD [Online] Mintel; Jul. 2002 (Jul. 2002) "Super Line Preventor+".
Database GNPD [Online] Mintel; Mar. 2003 (Mar. 2003) "Protek Performance Women's Shampoo Range".
Database GNPD [Online] Mintel; Sep. 2003 (Sep. 2003) "Retarding Body Hair Cream".
Database GNPD [Online] Mintel; Jan. 2002 (Jan. 2002) "Vitality Oxygen Complex Moisturizer".
Database GNPD [Online] Mintel; Sep. 2003 (Sep. 2003) "Straight and Sleek Conditioner".

* cited by examiner

*Primary Examiner* — Kyle A Purdy
(74) *Attorney, Agent, or Firm* — Abel Schillinger, LLP

(57) ABSTRACT

A combination comprising creatine and/or creatinine and/or a derivative thereof, phenoxyethanol and, optionally, glycerol. This Abstract is not intended to define the invention disclosed in the specification, nor intended to limit the scope of the invention in any way.

15 Claims, No Drawings

ACTIVE SUBSTANCE COMBINATION OF CREATINE AND/OR CREATININE AND PHENOXYETHANOL

CROSS-REFERENCE TO RELATED APPLICATIONS

The present application claims priority under 35 U.S.C. § 119 of German Patent Application No. 103 55 714.8, filed Nov. 26, 2003, the disclosure of which is expressly incorporated by reference herein in its entirety.

BACKGROUND OF THE INVENTION

1. Field of the Invention

The present invention relates to an active substance combination of creatine and/or creatine derivatives and/or creatinine and/or creatinine derivatives, phenoxyethanol and, optionally, glycerin, which can be advantageously used in cosmetic or dermatological preparations for the treatment and prophylaxis of the symptoms of UV-induced and/or ozone-induced skin damage and of inflammatory and degenerative skin conditions.

2. Discussion of Background Information

Cosmetic skin care means primarily the strengthening or rebuilding of the natural function of the skin as a barrier against environmental factors (e.g., dirt, chemicals, microorganisms) and against the loss of endogenous substances (e.g., water, natural fats, electrolytes). If this function is impaired, an intensified absorption of toxic or allergenic substances or an attack by microorganisms can occur, resulting in toxic or allergic skin reactions.

Another aim of skin care is to compensate for the loss by the skin of lipids and water caused by daily washing. This is particularly important if the natural regenerative ability is inadequate. Moreover, skin care products should protect against environmental factors, in particular sun and wind, and delay skin aging.

Chronological skin aging is caused, e.g., by endogenous, genetically determined factors. The following structural damage and functional disorders may arise, under the term "senile xerosis", e.g., in the epidermis and the dermis as a result of aging:

(a) Dryness, roughness and formation of fine lines due to dryness,
(b) Itching and
(c) Reduced regreasing by sebaceous glands (e.g., after washing).

Exogenous factors, such as UV light and chemical noxae, can have a cumulative effect and, e.g., accelerate or supplement the endogenous aging processes. In the epidermis and dermis, for example, the following structural damage and functional disorders occur in the skin, in particular due to exogenous factors; these are more far-reaching than the degree and quality of the damage in the case of chronological aging:

(d) Visible vascular dilation (telangiectases, cuperosis);
(e) Flaccidity and formation of wrinkles;
(f) Local hyperpigmentation, hypopigmentation and abnormal pigmentation (e.g., senile keratoses) and
(g) Increased susceptibility to mechanical stress (e.g., cracking).

The present invention relates in particular to products for the care of skin that has aged naturally and to the treatment of secondary damage of light aging, in particular the phenomena listed under a) through g).

Products for the care of aged skin are known per se. They contain, e.g., retinoids (vitamin A acid and/or derivatives thereof) or vitamin A and/or derivatives thereof. However, the degree of their effect on structural damage is limited. Moreover, in product development there are considerable difficulties in stabilizing the active substances sufficiently against oxidative decay. Moreover, the use of products containing vitamin A acid often causes severe erythematous skin irritations. Retinoids can therefore be used only in low concentrations.

The present invention relates in particular to cosmetic preparations which provide an effective protection against harmful oxidation processes in the skin, but also a protection of cosmetic preparations themselves or the protection of constituents of cosmetic preparations against harmful oxidation processes.

The harmful effect on the skin of the ultraviolet part of solar radiation is generally known. Whereas rays with a wavelength of less than 290 nm (the so-called UVC range) are absorbed by the ozone layer in the earth's atmosphere, rays in the range between about 290 nm and about 320 nm, the so-called UVB range, cause an erythema, a simple sunburn or even burns of greater or lesser severity.

The narrower range around 308 m is indicated to be the maximum of the erythematous effect of sunlight.

Numerous compounds are known for protecting against UVB radiation, which compounds are derivatives of 3-benzylidene camphor, 4-aminobenzoic acid, cinnamic acid, salicylic acid, benzophenone and 2-phenyl benzimidazole.

It is also important to have filter substances available for the range between approx. 320 nm and approx. 400 nm, the so-called UVA range, since the corresponding rays can cause reactions in photosensitive skin. It has been found that UVA radiation leads to damage of the elastic and collagen fibers of the connective tissue, which leads to premature aging of the skin, and that it should be considered the cause of numerous phototoxic and photoallergic reactions. The harmful effect of UVB radiation can be intensified by UVA radiation.

To protect against rays of the UVA region, therefore, certain derivatives of dibenzoylmethane are used, the photostability of which is inadequate (Int. J. Cosm. Science 10, 53 (1988), the entire disclosure whereof is expressly incorporated by reference herein).

Further, UV radiation can also lead to photochemical reactions, in which case the photochemical reaction products interfere with the metabolism of the skin.

Such photochemical reaction products are primarily free-radical compounds, e.g., hydroxyl radicals. Undefined free-radical photoproducts that can form in the skin itself can also cause uncontrolled secondary reactions due to their high reactivity. Furthermore, singlet oxygen, a non-free-radical excited state of the oxygen molecule, can also occur during UV radiation, as can short-lived epoxides and many others. Singlet oxygen, for example, differs from triplet oxygen (free-radical basic state) that is normally present by its increased reactivity. However, excited reactive (free-radical) triplet states of the oxygen molecule also exist.

Furthermore, UV radiation is a type of ionizing radiation. There is therefore the risk that ionic species will also form during UV exposure, which then for their part can interfere oxidatively with biochemical processes.

In order to prevent these reactions, additional antioxidants and/or free-radical scavengers can be incorporated into cosmetic or dermatological formulations.

It has already been proposed to use vitamin E, a substance with known antioxidant effect, in light-protection formulations, yet here too the effect obtained falls far short of the desired effect.

It would be advantageous to have available cosmetically, dermatologically and pharmaceutically active substances and preparations and light-protective formulations for the prophylaxis and treatment of light-sensitive skin, in particular photodermatoses, preferably PLD.

Further terms for polymorphous light dermatosis are PLD, PLE, Mallorca acne and numerous other terms as given in the literature (e.g., A. Voelckel et al., *Zentralblatt Haut-und Geschlechtskrankheiten* (1989), 156, p. 2, the entire disclosure whereof is expressly incorporated by reference herein).

Antioxidants are mainly used as protective substances against the deterioration of the preparations in which they are contained. However, it is known that undesirable oxidation processes can also occur in human and animal skin. Such processes play a substantial role in skin aging.

Oxidative damage to the skin and its more direct causes are described in the article *Skin Diseases Associated with Oxidative Injury* in *Oxidative Stress in Dermatology*, p. 323 ff. (Marcel Decker Inc., New York, Basel, Hong Kong, ed. Jürgen Fuchs, Frankfurt, and Lester Packer, Berkeley/California), the entire disclosure whereof is expressly incorporated by reference herein. Also, in order to prevent such reactions, antioxidants and/or free-radical scavengers may be additionally incorporated into cosmetic or dermatological formulations.

Several antioxidants and free-radical scavengers are known. For example, U.S. Pat. Nos. 4,144,325 and 4,248,861, the entire disclosures whereof are expressly incorporated by reference herein, and numerous other documents have already proposed the use of vitamin E, a substance with known antioxidant effect, in light-protection formulations. Nevertheless here, too, the effect obtained falls far short of the desired effect.

The advantageous prophylactic and therapeutic effect of creatine in cosmetic and medical skin care is known per se. Creatine (from the Greek: το κρεας ="the meat") is characterized by the following structure:

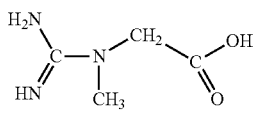

Creatine is found in the myoserum of vertebrates in amounts of 0.05-0.4%, in small amounts also in the brain and blood. As a monohydrate, it is a colorless, crystalline powder. In aqueous solution, creatinine is formed. In the organism, it is formed by the transamidination of L-arginine on glycine to afford guanidinoacetic acid, and subsequent methylation thereof by means of S-adenosyl methionine (by guanidinoacetate methyltransferase). Creatine is regarded as an appetite-promoting constituent of beef and meat extract. The addition of creatine to the diet enhances physical performance.

The prior art is extensive on the cosmetic and dermatological uses of creatine. Thus, DE 100 32 964, the entire disclosure whereof is expressly incorporated by reference herein, describes the use of creatine and/or creatine derivatives in cosmetic or dermatological preparations for the treatment and prophylaxis of the symptoms of UV-induced and/or ozone-induced skin damage and of inflammatory and degenerative skin conditions.

JP 2000/247,866, the entire disclosure whereof is expressly incorporated by reference herein, describes skin cosmetics with a content of creatine and/or creatinine which can be used as a cream or as a milky lotion, where excellent skin care properties are attributed to the relevant preparations.

Furthermore, WO 00/33787, the entire disclosure whereof is expressly incorporated by reference herein, describes the use of creatinine as an effective constituent of deodorants.

Moreover, EP-A-565 010, the entire disclosure whereof is expressly incorporated by reference herein, describes hair growth and hair dye preparations with a content of creatinine phosphate.

Finally, U.S. Pat. No. 4,590,067 and EP-A-178 602, the entire disclosures whereof are expressly incorporated by reference herein, describe the use of creatine or creatinine to produce preparations with anti-inflammatory effect.

However, there is the disadvantage that in aqueous products creatine and creatinine crystallize easily, whereby crystals with non-cosmetic impression form and the effectiveness of the product is reduced. This tendency to crystallize is intensified by water-soluble substances, the solubilization of which binds water that thus is no longer available for the solubilization of creatine, creatinine and/or derivatives thereof. Glycerin and phenoxyethanol are examples of compounds which intensify the tendency of water-soluble active substances to crystallize in cosmetic preparations such as hydrogels, W/O emulsions or O/W emulsions, which can result in a non-cosmetic appearance and/or a loss of effectiveness during storage or use.

It is desirable to find ways of avoiding the disadvantages of the prior art. In particular, the effect of eliminating the damage associated with endogenous, chronological and exogenous skin aging and the prophylaxis should be durable, sustained, and without the risk of side effects. It also is desirable to have available preparations which are safe with regard to any possible microbic contamination of the product.

It would further be advantageous to find a form of administering creatine that is characterized by a reduced tendency to form creatine crystals.

SUMMARY OF THE INVENTION

The present invention provides an active substance combination which comprises
    (a) creatine and/or creatinine and/or a creatine derivative and/or a creatinine derivative,
    (b) phenoxyethanol, and
    (c) optionally, glycerin.

In one aspect of the present combination, the weight ratio of creatinine to creatine may be from about 10:1 to about 1:10, e.g., from about 4:1 to about 3:7, or from about 2:1 to about 1:2.

In another aspect, the weight ratio (A:B:C) may be a:b:c, where a, b and c independently of one another represent rational numbers of from about 1 to about 200, e.g., from about 1 to about 50, and
    A represents the sum of creatine and creatinine
    B represents phenoxyethanol
    C represents glycerin.

In yet another aspect, the weight ratio (B+C)/A may be from about 0.5 to about 200, e.g., from about 1 to about 50.

In a still further aspect, the combination may comprise creatine phosphate.

The present invention also provides a cosmetic or dermatological preparation which comprises an effective amount of the active substance combination according to the present invention, including the various aspects thereof, as set forth above.

In one aspect, the preparation may comprise from about 0.0005% to about 50% by weight of the active substance combination, e.g., from about 0.01% to about 20% by weight, based on the total weight of the preparation.

In another aspect, the preparation may comprise from about 0.001% to about 10% by weight, e.g., from about 0.01% to about 1% by weight of creatine and/or a creatine derivative and/or the preparation may comprise from about 0.001% to about 10% by weight, e.g., from about 0.01% to about 1% by weight of creatinine and/or a creatinine derivative, based on the total weight of the preparation.

In yet another aspect, the preparation may comprise from about 0.001% to about 30% by weight, e.g., from about 0.01% to about 15% by weight, or from about 0.01% to about 15% by weight of glycerin, preferably from about 1% to about 7% by weight, based on the total weight of the preparation.

In a still further aspect, the preparation may comprise up to about 1% by weight of phenoxyethanol and/or at least about 0.01% by weight, e.g., at least about 0.1% by weight of phenoxyethanol, based on the total weight of the preparation.

The present invention also provides a cosmetic or dermatological preparation which comprises from about 0.01% to about 20% of an active substance combination. The active substance combination comprises
  (a) creatine and/or creatinine and/or a creatine derivative and/or a creatinine derivative,
  (b) phenoxyethanol, and
  (c) optionally, glycerin.

In one aspect of this preparation, the weight ratio of creatinine to creatine in the active substance combination may be from about 4:1 to about 3:7, e.g., from about 2:1 to about 1:2.

In another aspect, the weight ratio (A:B:C) may be a:b:c, where a, b and c independently of one another represent rational numbers of from about 1 to about 50, and
  A represents the sum of creatine and creatinine
  B represents phenoxyethanol and
  C represents glycerin.

In yet another aspect, the weight ratio (B+C)/A may be from about 1 to about 50.

In a still further aspect, the preparation may comprise from about 0.01% to about 1% by weight of creatine and/or a creatine derivative and/or from about 0.01% to about 1% by weight of creatinine and/or a creatinine derivative, based on the total weight of the preparation.

In a still further aspect, the preparation may comprise from about 0.01% to about 15% by weight of glycerin, e.g., about 0.01% to about 15% by weight, or from about 1% to about 7% by weight of glycerin, based on the total weight of the preparation.

The present invention also provides an O/W emulsion which comprises the active substance combination of the present invention, including the various aspects thereof, as set forth above.

The present invention also provides a method for the prophylaxis or treatment of skin aging, a method for the prophylaxis or treatment of dry skin and a method for the prophylaxis or treatment of abnormal skin pigmentation.

These methods comprise the application to at least a part of the skin of the preparation of the present invention, including the various aspects thereof.

If derivatives of creatine are used, the preferred derivative is creatine phosphate, which has the following structure:

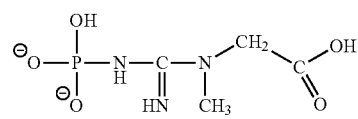

Creatine phosphate is present in fresh muscle where it plays an important role as an energy-storing phosphate (phosphagen). In the working muscle, adenosine 5'-triphosphate (ATP) and creatine are formed from creatine phosphate and adenosine 5'-diphosphate under the influence of the enzyme creatine kinase. In the resting muscle the reverse reaction takes place.

Additionally, creatine sulfate, creatine acetate, creatine ascorbate and the derivatives esterified on the carboxyl group with mono- or polyfunctional alcohols are further non-limiting examples of advantageous creatine derivatives for use in the present invention.

Creatinine (from the Greek: το κρεας ="the meat") is characterized by the following structure:

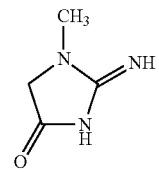

It is formed in the organism through nonenzymatic conversion of creatine phosphate according to the equation:

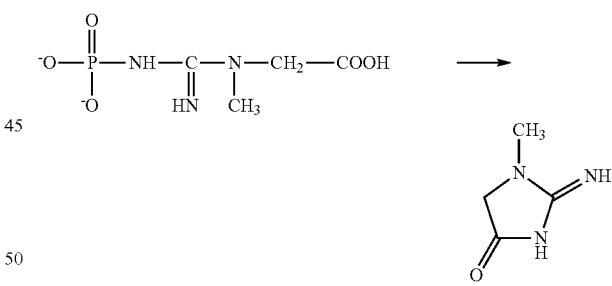

and is secreted through the kidneys. The amount of secreted creatinine is proportional to the muscle mass and is virtually constant for a respective individual. Creatinine is contained in meat extract and in meat broth cubes.

A cosmetic or dermatological preparation according to the invention preferably comprises from about 0.0001%, e.g., from about 0.001%, or from about 0.01% to about 10%, e.g., to about 1% by weight of creatinine and/or creatinine derivatives, based on the total weight of the preparation.

According to the present invention, creatine may advantageously be used without the presence of creatinine, and creatinine may advantageously be used without the presence of creatine. However, it is particularly advantageous to use both substances simultaneously in the active substance combinations and preparations according to the present invention, in particular if the weight ratio of creatinine to creatine is selected from about 10:1 to about 1:10, preferably from about 4:1 to about 3:7, more preferably from about 2:1 to about 1:2.

Phenoxyethanol is characterized by the chemical structure

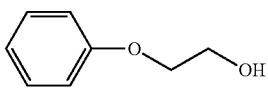

Phenoxyethanol is a viscous liquid with a light, slightly pleasant smell and an astringent taste. Phenoxyethanol is found in nature, inter alia, in tropical fruit, in cichorium endiva and in green tea (camellia sinesis). It has a mild, rose-like scent and is also used as a fixative for perfume compositions. It is miscible with acetone, ethyl alcohol and glycerin and is soluble in water and fats, e.g., olive oil and peanut oil.

Phenoxyethanol is effective above all in acidic and neutral, as well as in an alkaline media and is completely non-toxic. It provides sufficient protection already in low concentrations. Due to its good tolerability together with its excellent effectiveness it was quickly adopted in the pharmaceutical and cosmetic industry.

The use of glycerin in cosmetics is generally known. Glycerin has a skin-moisturizing and skin-smoothing effect and is a constituent of many skin care cosmetic preparations.

According to the invention, it is very advantageous to use glycerin. A preparation according to the invention advantageously contains from about 0.001%, e.g., preferably from about 0.01%, more preferably from about 1%, to about 30% by weight, preferably to about 15% by weight, more preferably to about 7% by weight of glycerin, based on the total weight of the preparation.

It may also be advantageous if the preparation according to the invention is characterized by a weight ratio of (A:B:C) of a:b:c, where a, b and c independently of one another represent positive rational numbers from about 1 to about 200, preferably from about 1 to about 50 and A represents the sum of the weight units of creatine and creatinine (e.g., in % by weight)
B represents the weight units of phenoxyethanol and
C represents the weight units of glycerin,
based on the total weight of the preparation.

Furthermore, it has proven advantageous to select the ratio (B+C)/A where A, B, and C are as defined above in the range of from about 0.5 to about 200, preferably from about 1 to about 50.

According to the invention, the active substance combination is preferably used in cosmetic or dermatological preparations in a concentration of from about 0.0005%, e.g., from about 0.01%, to about 50%, e.g., to about 20% by weight, based on the total weight of the preparation.

The active substance combinations used according to the invention can readily be incorporated into customary cosmetic or dermatological formulations, for example, in emulsions, pump sprays, aerosol sprays, aerosol emulsion foams, creams, ointments, tinctures, lotions, nail care products (e.g., nail polishes, nail polish removers, nail balms) and the like.

It is also possible and may be advantageous to combine the active substance combination according to the invention with other active substances, e.g., with other antimicrobially, antimycotically or antivirally active substances.

It is advantageous to buffer the compositions according to the invention. A pH range of from about 3.5 to about 8.0 is advantageous. It is particularly advantageous to select the pH in a range of from about 6.5 to about 8.0.

The cosmetic and/or dermatological formulations of the present invention may have a conventional composition and can be used to treat the skin and/or the hair in terms of a dermatological treatment or a treatment in terms of cosmetic care. However, they can also be used in cosmetic products for decorative cosmetics.

Accordingly, cosmetic and/or topical dermatological compositions of the present invention, depending on their structure, can be used, for example, as a skin care product, a skin protection product, a cleansing product, a sunscreen product, a hair pack, a body cleansing product, for day or night treatment, and for the care of certain skin areas, such as hands, face, feet, etc.

The use of the preparations according to the invention for the prophylaxis and treatment of the symptoms of aging skin, to prevent and reduce the development and spread of fine lines and wrinkles and for the treatment and care of aged skin is also within the scope of the present invention.

Furthermore, the use of the preparations according to the invention is also preferred for the prophylaxis and treatment of the symptoms of dry skin. Non-limiting examples of suitable additional active substances for this purpose are: natural oils (sunflower oil, evening primrose oil, jojoba oil, macademia nut oil, castor oil), ceramides, in particular ceramide I, III and VI, cholesterol, phytosterols, fatty acids with a chain length of about $C_{16-26}$, carnitine and derivatives thereof, urea, polyols such as glycerin, butylene glycol, propylene glycol and dipropylene glycol, pseudoceramides; electrolytes such as sodium chloride and taurine, fatty alcohols and waxes.

Moreover, the use of preparations according to the invention is advantageous for the prophylaxis and treatment of the symptoms of skin with abnormal pigmentation. Preferred additional active substances for this purpose include: tyrosinase inhibitors, azelaic acid, hydroquinone derivatives, dioic acid, lipoic acid and derivatives thereof, and kojic acid.

The use of the cosmetic and/or dermatological preparations according to the invention for the prophylaxis, treatment and cleansing of oily skin and/or for the prophylaxis and treatment of blemished skin and/or of cellulite is also within the scope of the present invention.

For use, the cosmetic and/or dermatological preparations are applied in a sufficient quantity to the skin and/or the hair in the usual manner for cosmetics and dermatological products.

Cosmetic and dermatological preparations that are present in the form of a sunscreen are also advantageous. In addition, they advantageously contain at least one UVA filter and/or at least one UVB filter and/or at least one inorganic pigment.

Cosmetic preparations according to the invention can be present in various forms, as they are, e.g., normally used for this type of preparation. Thus they can be present in the form of, e.g., a solution, an emulsion of the water-in-oil (W/O) type or oil-in-water (O/W) type, a multiple emulsion, e.g., of the water-in-oil-in-water (W/O/W) type, a gel, a hydrodispersion, a solid stick or an aerosol.

The cosmetic preparations according to the invention may contain cosmetic auxiliaries, e.g., selected from those which are customarily used in such preparations. Non-limiting examples thereof include preservatives, bactericides, antioxidants, perfumes, antifoams, dyes, pigments that have a coloring effect, thickeners, surface-active substances, emulsifiers, emollients, moisturizers and/or humectants, fats, oils, waxes and other customary constituents of a cosmetic formulation, such as, e.g., alcohols, polyols, polymers, foam stabilizers, electrolytes, organic solvents and silicone derivatives.

If the cosmetic or dermatological preparation is present in the form of a solution or a lotion, non-limiting examples of solvents that may be used include:
  water or aqueous solutions;
  oils, such as triglycerides of capric or caprylic acid, fatty acid ethers such as dicaprylyl ether, carbonic acid esters such as dicaprylyl carbonate, and vegetable triglycerides such as sunflower oil;
  fats, waxes and other natural and synthetic adipoids, preferably esters of fatty acids with alcohols of low carbon number, e.g., with isopropanol, propylene glycol or glycerin, and esters of fatty alcohols with alkanoic acids of low carbon number or with fatty acids;
  alcohols, diols or polyols of low carbon number and ethers thereof, preferably ethanol, isopropanol, propylene glycol, glycerin, ethylene glycol, ethylene glycol monoethyl or monobutyl ether, propyleneglycol monomethyl, monoethyl or monobutyl ether, diethylene glycol monomethyl or monoethyl ether, ethylhexylglycerin, methylpropandiol and analogous products.

In particular, mixtures of the above solvents may be used. In the case of alcoholic solvents, water may be a further constituent.

Antioxidants which are suitable or customary for cosmetic and/or dermatological uses are non-limiting examples of beneficial antioxidants that can be used for the purposes of the invention.

The antioxidants for use in the present invention are advantageously selected from amino acids (e.g., glycine, histidine, tyrosine, tryptophan) and derivatives thereof, imidazoles (e.g., urocanic acid) and derivatives thereof, peptides, such as D,L-carnosine, D-carnosine, L-carnosine and derivatives thereof (e.g., anserine), carotenoids, carotenes (e.g., α-carotene, β-carotene, lycopene) and derivatives thereof, lipoic acid and derivatives thereof (e.g., dihydrolipoic acid), aurothioglucose, propylthiouracil and other thiols (e.g., thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulfoximine compounds (e.g., buthionine sulfoximines, homocysteine sulfoximine, buthionine sulfones, penta-, hexa-, heptathionine sulfoximine) in very low tolerated doses (e.g., pmol to µmol/kg), and (metal) chelating agents (e.g., α-hydroxy fatty acids, palmitic acid, phytic acid, lactoferrin), α-hydroxy acids (e.g., citric acid, lactic acid, malic acid), humic acid, bile acid, bile extracts, bilirubin, biliverdin, EDTA, EGTA and derivatives thereof, unsaturated fatty acids and derivatives thereof (e.g., γ-linolenic acid, linoleic acid, oleic acid), folic acid and derivatives thereof, ubiquinone and ubiquinole and derivatives thereof, vitamin C and derivatives (e.g., ascorbyl palmitate, Mg ascorbyl phosphate, ascorbyl acetate) tocopherols and derivatives (e.g., vitamin E acetate), vitamin A and derivatives (vitamin A palmitate) and coniferyl benzoate of benzoin resin, rutinic acid and derivatives thereof, ferulic acid and derivatives thereof, butylated hydroxytoluene, butylated hydroxyanisole, nordihydroguaiacic acid, nordihydroguaiaretic acid, trihydroxybutyrophenone, uric acid and derivatives thereof, mannose and derivatives thereof, zinc and derivatives thereof (e.g., ZnO, $ZnSO_4$), selenium and derivatives thereof (e.g., selenomethionine), stilbenes and derivatives thereof (e.g., stilbene oxide, trans-stilbene oxide) and the derivatives (salts, esters, ethers, sugars, nucleotides, nucleosides, peptides and lipids) of these active substances that are suitable for the purposes of the present invention.

The amount of antioxidants (one or more compounds) in the preparations of the present invention is preferably from about 0.001% to about 30% by weight, more preferably from about 0.05% to about 20% by weight, in particular from about 0.1 to about 10% by weight, based on the total weight of the preparation.

The cosmetic preparations according to the invention may contain cosmetic auxiliaries, such as are customarily used in such preparations, for example, preservatives, bactericides, deodorizing substances, antiperspirants, insect repellants, vitamins, antifoams, dyes, coloring pigments, thickeners, emollients, moisturizers and/or humectants, fats, oils, waxes and other customary constituents of a cosmetic formulation such as, e.g., alcohols, polyols, polymers, foam stabilizers, electrolytes, organic solvents and silicone derivatives.

Preparations according to the invention may also advantageously contain substances that absorb UV radiation in the UVB range, the total amount of the filter substances being, e.g., from about 0.1% by weight to about 30% by weight, preferably from about 0.5% to about 10% by weight, in particular from about 1% to about 6% by weight, based on the total weight of the preparations, in order to make available cosmetic preparations that protect the hair or the skin from the entire range of ultraviolet radiation. They may also be used as sunscreen for the hair.

If the preparations according to the invention contain UVB filter substances, these can be oil-soluble or water-soluble. Examples of advantageous oil-soluble UVB filters according to the invention are:
  3-benzylidenecamphor und derivatives thereof, preferably 3-(4-methylbenzylidene)-camphor,
  4-aminobenzoic acid derivatives, preferably 2-ethylhexyl 4-(dimethylamino)-benzoate, amyl 4-(dimethylamino) benzoate;
  esters of cinnamic acid, preferably 2-ethylhexyl 4-methoxycinnamate, isopentyl 4-methoxycinnamate;
  esters of salicylic acid, preferably 2-ethylhexyl salicylate, 4-isopropylbenzyl salicylate, homomenthyl salicylate;
  derivatives of benzophenone, preferably 2-hydroxy-4-methoxybenzophenone, 2-hydroxy-4-methoxy-4'-methylbenzophenone, 2,2'-dihydroxy-4-methoxybenzophenone;
  esters of benzalmalonic acid, preferably di(2-ethylhexyl) 4-methoxybenzalmalonate;
  2,4,6-trianilino-(p-carbo-2'-ethyl-1'-hexyloxy)-1,3,5-triazine.

Examples of advantageous water-soluble substances are:
  salts of 2-phenylbenzimidazole-5-sulfonic acid such as, e.g., the sodium, potassium and triethanolammonium salts thereof, and the sulfonic acid itself,
  sulfonic acid derivatives of benzophenones, preferably 2-hydroxy-4-methoxybenzophenone-5-sulfonic acid and the salts thereof;
  sulfonic acid derivatives of 3-benzylidene camphor, such as, e.g., 4-(2-oxo-3-bornylidenemethyl)benzene sulfonic acid, 2-methyl-5-(2-oxo-3-bornylidenemethyl) sulfonic acid and the salts thereof, and 1,4-di(2-oxo-10-sulfo-3-bornylidenemethyl)-benzene and the salts thereof (the corresponding 10-sulfato compounds, e.g., the corresponding sodium, potassium or triethanol ammonium salts), also known as benzene-1,4-di(2-oxo-3-bornylidenemethyl-10-sulfonic acid.

The above list of UVB filters that can be used in combination with the active substance combination according to the invention is of course not intended to be limiting.

The present invention also contemplates the use of a combination of the emulsions according to the invention with at least one UVB filter as an antioxidant or the use of a combination of the active substance combination according to the invention with at least one UVB filter as an antioxidant in a cosmetic or dermatological preparation.

It may also be advantageous to use UVA filters that are customarily contained in cosmetic preparations. These substances are preferably derivatives of dibenzoylmethane, in particular 1-(4'-tert-butylphenyl)-3-(4'-methoxyphenyl)-propane-1,3-dione and 1-phenyl-3-(4'-isopropylphenyl)propane-1,3-dione.

Further advantageous UVA filters belong to the group of triazines such as, e.g., 2,4-bis-{[4-(2-ethyl-hexyloxy)-2-hydroxyl]-phenyl}-6-(4-methoxyphenyl)-1,3,5-triazine (trade name Tinosorb® S) and to the group of triazoles, such as, e.g., 2,2'-methylene-bis-[6-2H-benzotriazole-2yl]-4-(1,1,3,3-tetramethylbutyl)phenol) (trade name Tinosorb® M). An advantageous water-soluble UVA filter is 2'-bis-(1,4-phenylene)-1H-benzimidazole-4,6-disulfonic acid-sodium salt (trade name Neo Heliopan AP®). The quantities used for the UVB combinations as indicated above can be used here as well.

Preferred inorganic pigments are metal oxides and/or other metal compounds that are poorly soluble in water or insoluble in water, in particular oxides of titanium ($TiO_2$), zinc (ZnO), iron (e.g., $Fe_2O_3$), zirconium ($ZrO_2$), silicon ($SiO_2$), manganese (e.g., MnO), aluminum ($Al_2O_3$), cerium (e.g., $Ce_2O_3$), mixed oxides of the corresponding metals and mixtures of such oxides, as well as barium sulfate ($BaSO_4$).

According to the present invention the pigments can also advantageously be used in the form of commercially available oily or aqueous predispersions. Advantageously, dispersion aids and/or solubilizers may be added to these predispersions.

The pigments for use in the present invention may advantageously be surface-treated ("coated"), where, e.g., a hydrophilic, amphiphilic or hydrophobic character is to be formed or retained. This surface treatment may include that the pigments are provided with a thin hydrophilic and/or hydrophobic inorganic and/or organic layer according to procedures known per se. The various surface coatings within the scope of the present invention may also contain water.

Within the scope of the present invention inorganic surface coatings may comprise, for example, aluminum oxide ($Al_2O_3$), aluminum hydroxide $Al(OH)_3$, or alumina hydrate (also: alumina, CAS no.: 1333-84-2), sodium hexametaphosphate ($NaPO_3)_6$, sodium metaphosphate ($NaPO_3)_n$, silicon dioxide ($SiO_2$) (also: silica, CAS no.: 7631-86-9), or iron oxide ($Fe_2O_3$). These inorganic surface coatings can be present individually, in combination and/or in combination with organic coating materials.

Organic surface coatings within the scope of the present invention may comprise, for example, vegetable or animal aluminum stearate, vegetable or animal stearic acid, lauric acid, dimethylpolysiloxane (also: dimethicone), methylpolysiloxane (methicone), simethicone (a mixture of dimethylpolysiloxane with an average chain length of about 200 to about 350 dimethylsiloxane units and silica gel) or alginic acid. These organic surface coatings may be used individually, in combination and/or in combination with inorganic coating materials.

Zinc oxide particles and predispersions of zinc oxide particles that are suitable according to the invention can be obtained under the following trade names from the listed companies:

| Trade name | Coating | Manufacturer |
| --- | --- | --- |
| Z-Cote HP1 | 2% dimethicone | BASF |
| Z-Cote | / | BASF |
| ZnO NDM | 5% dimethicone | H&R |

Suitable titanium dioxide particles and predispersions of titanium dioxide particles can be obtained under the following trade names from the listed companies:

| Trade name | Coating | Manufacturer |
| --- | --- | --- |
| MT-100TV | Aluminium hydroxide/stearic acid | Tayca Corporation |
| MT-100Z | Aluminium hydroxide/stearic acid | Tayca Corporation |
| Eusolex T-2000 | Alumina/simethicone | Merck KgaA |
| Titanium dioxide T805 (Uvinul $TiO_2$) | Octyltrimethylsilane | Degussa |

Especially if crystalline or microcrystalline solids, e.g., inorganic micropigments, are to be incorporated into the preparations according to the invention, preparations according to the invention can also contain anionic, nonionic and/or amphoteric surfactants. Surfactants are amphiphilic materials that can dissolve organic, nonpolar substances in water.

The hydrophilic portions of a surfactant molecule are mostly polar functional groups, e.g., $—COO^-$, $—OSO_3^-$, $—SO_3^-$, whereas the hydrophobic parts as a rule are nonpolar hydrocarbon radicals. In general, surfactants are classified according to the type and charge of the hydrophilic part of the molecule. Four groups can be distinguished:
  anionic surfactants,
  cationic surfactants,
  amphoteric surfactants and
  nonionic surfactants.

Anionic surfactants usually have, as functional groups, carboxylate, sulphate or sulphonate groups. In aqueous solution, they form negatively charged organic ions in acidic or neutral media. Cationic surfactants are characterized almost exclusively by the presence of a quaternary ammonium group. In aqueous solution they form positively charged organic ions in acidic or neutral media. Amphoteric surfactants contain both anionic and cationic groups and accordingly in aqueous solution they behave like anionic or cationic surfactants, depending on the pH value. In strongly acidic media they have a positive charge, and in alkaline media they have a negative charge. By contrast, in the neutral pH range, they are zwitterionic, as the following example illustrates:

$RNH_2^+CH_2CH_2COOH\ X^-$ (at pH=2) $X^-$=any anion, e.g. $Cl^-$
$RNH_2^+CH_2CH_2COO^-$ (at pH=7)
$RNHCH_2CH_2COO^-B^+$ (at pH=12) $B^+$=any cation, e.g. $Na^+$ Polyether chains are typical of nonionic surfactants. Nonionic surfactants do not form ions in an aqueous medium.

A. Anionic Surfactants

Non-limiting examples of anionic surfactants which can be used advantageously include Acylamino acids (and salts thereof), such as
1. acyl glutamates, for example sodium acyl glutamate, di-TEA-palmitoyl aspartate and sodium caprylic/capric glutamate,
2. acyl peptides, for example palmitoyl-hydrolysed milk protein, sodium cocoyl-hydrolysed soy protein and sodium/potassium cocoyl-hydrolysed collagen,
3. sarcosinates, for example myristoyl sarcosinate, TEA-lauroyl sarcosinate, sodium lauroyl sarcosinate and sodium cocoyl sarcosinate,
4. taurates, for example sodium lauroyl taurate and sodium methyl cocoyl taurate,
5. acyl lactylates, lauroyl lactylate, caproyl lactylate
6. alaninates Carboxylic acids and derivatives thereof, such as
1. Carboxylic acids, for example lauric acid, aluminium stearate, magnesium alkanolate and zinc undecylenate,
2. ester carboxylic acids, for example calcium stearoyl lactylate, laureth-6 citrate and sodium PEG-4 lauramide carboxylate,
3. ether carboxylic acids, for example sodium laureth-13 carboxylate and sodium PEG-6 cocamide carboxylate, Phosphoric acid esters and salts, such as, for example, DEA-oleth-10-phosphate and dilaureth-4 phosphate, Sulfonic acids and salts, such as
1. acyl-isethionates, e.g. sodium/ammonium cocoyl isethionate,
2. alkylaryl sulfonates,
3. alkyl sulfonates, for example sodium cocomonoglyceride sulfate, sodium $C_{12-14}$-olefin sulfonate, sodium lauryl sulfoacetate and magnesium PEG-3 cocamide sulfate,
4. sulfosuccinates, for example, dioctyl sodium sulfosuccinate, disodium laureth sulfosuccinate, disodium lauryl sulfosuccinate and disodium undecyleneamido-MEA sulfosuccinate and Sulfuric acid esters, such as
1. alkyl ether sulfate, for example sodium, ammonium, magnesium, MIPA, TIPA laureth sulfate, sodium myreth sulfate and sodium $C_{12-13}$ pareth sulfate,
2. alkyl sulfates, for example sodium, ammonium and TEA lauryl sulfate.

B. Cationic Surfactants

Non-limiting examples of cationic surfactants which can be used advantageously include
1. alkylamines,
2. alkylimidazoles,
3. ethoxylated amines and
4. quaternary surfactants,
5. ester quats Quaternary surfactants contain at least one N atom which is covalently bound to 4 alkyl or aryl groups. Irrespective of the pH value, this results in a positive charge. Alkylbetaine, alkylamidopropylbetaine and alkylamidopropylhydroxysulfaine are advantageous. The cationic surfactants used according to the invention may also preferably be chosen from quaternary ammonium compounds, in particular benzyltrialkylammonium chlorides or bromides, such as, for example, benzyldimethylstearylammonium chloride, and also alkyltrialkylammonium salts, for example cetyltrimethylammonium chloride or bromide, alkyldimethylhydroxyethylammonium chlorides or bromides, dialkyldimethylammonium chlorides or bromides, alkylamidoethyltrimethylammonium ether sulfates, alkylpyridinium salts, for example lauryl or cetylpyridinium chloride, imidazoline derivatives and compounds having cationic character, such as amine oxides, for example alkyldimethylamine oxides or alkylaminoethyldimethylamine oxides. The use of cetyltrimethylammonium salts is particularly advantageous.

C. Amphoteric Surfactants

Non-limiting examples of amphoteric surfactants which can be used advantageously include
1. acyl/dialkylethylenediamine, for example, sodium acyl amphoacetate, disodium acyl amphodipropionate, disodium alkyl amphodiacetate, sodium acyl amphohydroxypropylsulfonate, disodium acyl amphodiacetate and sodium acyl amphopropionate,
2. N-alkylamino acids, for example aminopropylalkylglutamide, alkylaminopropionic acid, sodium alkylimidodipropionate and lauroamphocarboxyglycinate.

D. Nonionic Surfactants

Nonionic surfactants which can be used advantageously are
1. alcohols,
2. alkanolamides, such as cocamides MEA/DEA/MIPA,
3. amine oxides, such as cocoamidopropylamine oxide,
4. esters which are formed by esterification of carboxylic acids with ethylene oxide, glycerol, sorbitan or other alcohols,
5. ethers, for example ethoxylated/propoxylated alcohols, ethoxylated/propoxylated esters, ethoxylated/propoxylated glycerol esters, ethoxylated/propoxylated cholesterols, ethoxylated/propoxylated triglyceride esters, ethoxylated/propoxylated lanolin, ethoxylated/propoxylated polysiloxanes, propoxylated POE ethers and alkyl polyglycosides, such as lauryl glucoside, decyl glycoside and cocoglycoside.
6. sucrose esters, sucrose ethers
7. polyglycerol esters, diglycerol esters, monoglycerol esters
8. methylglucose esters, esters of hydroxy acids.

Also advantageous is the use of a combination of anionic and/or amphoteric surfactants with one or more nonionic surfactants.

The surface-active substance may be present in the preparation according to the invention in a concentration of from about 1% to about 95% by weight, based on the total weight of the preparation.

The lipid phase of the cosmetic or dermatological emulsions according to the invention may advantageously be selected from the following:

Mineral oils, mineral waxes

Oils, such as triglycerides of capric acid or caprylic acid, as well as natural oils, such as, e.g., castor oil;

Fats, waxes and other natural and synthetic fatty substances, preferably esters of fatty acids with alcohols of low carbon number, e.g., with isopropanol, propylene glycol or glycerin, or esters of fatty alcohols with alkanoic acids of low carbon number or with fatty acids;

Alkyl benzoates;

Silicone oils, such as dimethylpolysiloxanes, diethylpolysiloxanes, diphenylpolysiloxanes and mixed forms thereof.

The oil phase of the emulsions of the present invention is advantageously chosen from esters of saturated and/or unsaturated, branched and/or unbranched alkanecarboxylic acids having a chain length of from about 3 to about 30 carbon atoms and saturated and/or unsaturated, branched and/or unbranched alcohols having a chain length of from about 3 to about 30 carbon atoms, from the group of esters of aromatic carboxylic acids and saturated and/or unsaturated, branched and/or unbranched alcohols having a chain length of from about 3 to about 30 carbon atoms. Such ester oils can, for example, advantageously be chosen from isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate, and synthetic, semisynthetic and natural mixtures of such esters, e.g., jojoba oil.

The oil phase may also advantageously be chosen from branched and unbranched hydrocarbons and hydrocarbon waxes, silicone oils, dialkyl ethers, the group of saturated or unsaturated, branched or unbranched alcohols, and fatty acid triglycerides, namely the triglycerol esters of saturated and/or unsaturated, branched and/or unbranched alkanecarboxylic acids having a chain length of from about 8 to about 24 carbon atoms, in particular from about 12 to about 18 carbon atoms. The fatty acid triglycerides may, for example, advantageously be chosen from synthetic, semisynthetic and natural oils, e.g., olive oil, sunflower oil, soya oil, peanut oil, rapeseed oil, almond oil, palm oil, coconut oil, palm kernel oil and the like.

Any mixtures of such oil and wax components may also be used advantageously for the purposes of the present invention. In some instances, it may also be advantageous to use waxes, for example cetyl palmitate, as the sole lipid component of the oil phase.

The oil phase may particularly advantageously be chosen from 2-ethylhexyl isostearate, octyldodecanol, isotridecyl isononanoate, isoeicosane, 2-ethylhexyl cocoate, $C_{12-15}$-alkyl benzoate, caprylic/capric triglyceride, dicaprylyl ether and combinations of two or more thereof.

Particularly advantageous mixtures are those of $C_{12-15}$-alkyl benzoate and 2-ethylhexyl isostearate, those of $C_{12-15}$-alkyl benzoate and isotridecyl isononanoate, and those of $C_{12-15}$-alkyl benzoate, 2-ethylhexyl isostearate and isotridecyl isononanoate.

Of the hydrocarbons, paraffin oil, squalane and squalene may particularly advantageously be used for the purposes of the present invention.

Advantageously, the oil phase may also have a content of cyclic or linear silicone oils, or may be composed entirely of such oils, although it is preferred to use an additional content of other oil phase components apart from the silicone oil or the silicone oils.

Cyclomethicone (e.g., decamethylcyclopentasiloxane) is particularly advantageously used as the silicone oil for use in the present invention. However, other silicone oils can also be used advantageously for the purposes of the present invention, for example, undecamethylcyclotrisiloxane, polydimethylsiloxane and poly(methylphenylsiloxane).

Mixtures of cyclomethicone and isotridecyl isononanoate, and of cyclomethicone and 2-ethylhexyl isostearate are also particularly advantageous.

Optionally, the aqueous phase of the preparations according to the invention may advantageously contain:
  alcohols, diols or polyols of low carbon number, and ethers thereof, preferably ethanol, isopropanol, propylene glycol, glycerin, ethylene glycol, ethylene glycol monoethyl or monobutyl ether, propylene glycol monomethyl, monoethyl or monobutyl ether, diethylene glycol monomethyl or monobutyl ether and analogous products, and also alcohols of low carbon number, e.g., ethanol, isopropanol, 1,2-propanediol, glycerin and, in particular, one or more thickeners which can advantageously be chosen from the group of silicon dioxide, aluminum silicates, polysaccharides and derivatives thereof, e.g. hyaluronic acid, xanthan gum, hydroxypropylmethylcellulose, particularly advantageously from the group of polyacrylates, preferably a polyacrylate from the group of so-called carbopols, for example, carbopol grades 980, 981, 1382, 2984, 5984, in each case individually or in combination.

Preparations according to the invention which are present in the form of emulsions contain one or more emulsifiers. O/W emulsifiers may advantageously be chosen, for example, from the group of polyethoxylated, polypropoxylated or polyethoxylated and polypropoxylated products, e.g.:

fatty alcohol ethoxylates,
ethoxylated wool wax alcohols,
polyethylene glycol ethers of the general formula R—O—(—CH$_2$—CH$_2$—O—)$_n$—R',
fatty acid ethoxylates of the general formula R—COO—(—CH$_2$—CH$_2$—O—)$_n$—H, etherified fatty acid ethoxylates of the general formula R—COO—(—CH$_2$—CH$_2$—O—)$_n$—R', esterified fatty acid ethoxylates of the general formula R—COO—(—CH$_2$—CH$_2$—O—)$_n$—C(O)—R', polyethylene glycol glycerol fatty acid esters,
ethoxylated sorbitan esters,
cholesterol ethoxylates,
ethoxylated triglycerides,
alkyl ether carboxylic acids of the general formula R—O—(—CH$_2$—CH$_2$—O—)$_n$—CH$_2$—COOH where $n$ is a number of from about 5 to about 30,
polyoxyethylene sorbitol fatty acid esters,
alkyl ether sulfates of the general formula R—O—(—CH$_2$—CH$_2$—O—)$_n$—SO$_3$—H, fatty alcohol propoxylates of the general formula R—O—(—CH$_2$—CH(CH$_3$)—O—)$_n$—H, polypropylene glycol ethers of the general formula R—O—(—CH$_2$—CH(CH$_3$)—O—)$_n$—R', propoxylated wool wax alcohols,
etherified fatty acid propoxylates R—COO—(—CH$_2$—CH(CH$_3$)—O—)$_n$—R', esterified fatty acid propoxylates of the general formula R—COO—(—CH$_2$—CH(CH$_3$)—O—)$_n$—C(O)—R', fatty acid propoxylates of the general formula R—COO—(—CH$_2$—CH(CH$_3$)—O—)$_n$—H, polypropylene glycol glycerol fatty acid esters,
propoxylated sorbitan esters,
cholesterol propoxylates,
propoxylated triglycerides,
alkyl ether carboxylic acids of the general formula R—O—(—CH$_2$—CH(CH$_3$)O—)$_n$—CH$_2$—COOH, alkyl ether sulfates or the parent acids of these sulfates of the general formula R—O—(—CH$_2$—CH(CH$_3$)—O—)$_n$—SO$_3$—H, fatty alcohol ethoxylates/propoxylates of the general formula R—O—X$_n$—Y$_m$—H, polypropylene glycol ethers of the general formula R—O—X$_n$—Y$_m$—R', etherified fatty acid propoxylates of the general formula R—COO—X$_n$—Y$_m$—R', fatty acid ethoxylates/propoxylates of the general formula R—COO—X$_n$—Y$_m$—H.

According to the invention, the polyethoxylated or polypropoxylated or polyethoxylated and polypropoxylated O/W emulsifiers used are particularly advantageously chosen from the group of substances having HLB values of from about 11 to about 18, very particularly advantageously having HLB values of from about 14.5 to about 15.5, provided the O/W emulsifiers have saturated radicals R and R'. If the O/W emulsifiers have unsaturated radicals R and/or R', or isoalkyl derivatives are present, the preferred HLB values of such emulsifiers may also be lower or higher.

It is advantageous to choose the fatty alcohol ethoxylates from ethoxylated stearyl alcohols, cetyl alcohols, cetylstearyl alcohols (cetearyl alcohols). Particular preference is given to:
polyethylene glycol(13) stearyl ether (steareth-13), polyethylene glycol(14) stearyl ether (steareth-14), polyethylene glycol(15) stearyl ether (steareth-15), polyethylene glycol(16) stearyl ether (steareth-16), polyethylene glycol(17) stearyl ether (steareth-17), polyethylene glycol(18) stearyl ether (steareth-18), polyethylene glycol (19) stearyl ether (steareth-19), polyethylene glycol (20) stearyl ether (steareth-20),
polyethylene glycol(12) isostearyl ether (isosteareth-12), polyethylene glycol (13) isostearyl ether (isosteareth-13), polyethylene glycol(14) isostearyl ether (isosteareth-14), polyethylene glycol(15) isostearyl ether (isosteareth-15), polyethylene glycol(16) isostearyl ether (isosteareth-16), polyethylene glycol(17) isostearyl ether (isosteareth-17), polyethylene glycol(18) isostearyl ether (isosteareth-18), polyethylene glycol (19) isostearyl ether (isosteareth-19), polyethylene glycol(20) isostearyl ether (isosteareth-20),
polyethylene glycol(13) cetyl ether (ceteth-13), polyethylene glycol(14) cetyl ether (ceteth-14), polyethylene glycol(15) cetyl ether (ceteth-15), polyethylene glycol (16) cetyl ether (ceteth-16), polyethylene glycol(17) cetyl ether (ceteth-17), polyethylene glycol(18) cetyl ether (ceteth-18), polyethylene glycol(19) cetyl ether (ceteth-19), polyethylene glycol(20) cetyl ether (ceteth-20),
polyethylene glycol(13) isocetyl ether (isoceteth-13), polyethylene glycol(14) isocetyl ether (isoceteth-14), polyethylene glycol(15) isocetyl ether (isoceteth-15), polyethylene glycol(16) isocetyl ether (isoceteth-16), polyethylene glycol(17) isocetyl ether (isoceteth-17), polyethylene glycol(18) isocetyl ether (isoceteth-18), polyethylene glycol(19) isocetyl ether (isoceteth-19), polyethylene glycol(20) isocetyl ether (isoceteth-20),
polyethylene glycol(12)oleyl ether (oleth-12), polyethylene glycol(13)oleyl ether (oleth-13), polyethylene glycol(14)oleyl ether (oleth-14), polyethylene glycol(15) oleyl ether (oleth-15),
polyethylene glycol(12)lauryl ether (laureth-12), polyethylene glycol(12)isolauryl ether (isolaureth-12),
polyethylene glycol(13)cetylstearyl ether (ceteareth-13), polyethylene glycol(14)cetylstearyl ether (ceteareth-14), polyethylene glycol(15)cetylstearyl ether (ceteareth-15), polyethylene glycol(16)cetylstearyl ether (ceteareth-16), polyethylene glycol(17)cetylstearyl ether (ceteareth-17), polyethylene glycol(18)cetylstearyl ether (ceteareth-18), polyethylene glycol(19) cetylstearyl ether (ceteareth-19), polyethylene glycol (20)cetylstearyl ether (ceteareth-20).

It is also advantageous to choose the fatty acid ethoxylates from the following group:
polyethylene glycol(20)stearate, polyethylene glycol(21) stearate, polyethylene glycol(22)stearate, polyethylene glycol(23)stearate, polyethylene glycol(24)stearate, polyethylene glycol(25)stearate,
polyethylene glycol(12)isostearate, polyethylene glycol (13)isostearate, polyethylene glycol(14)isostearate, polyethylene glycol(15)isostearate, polyethylene glycol(16)isostearate, polyethylene glycol(17)isostearate, polyethylene glycol(18)isostearate, polyethylene glycol(19)isostearate, polyethylene glycol(20)isostearate, polyethylene glycol(21)isostearate, polyethylene glycol(22)isostearate, polyethylene glycol(23)isostearate, polyethylene glycol(24)isostearate, polyethylene glycol(25)isostearate,
polyethylene glycol(12)oleate, polyethylene glycol(13) oleate, polyethylene glycol(14)oleate, polyethylene glycol(15)oleate, polyethylene glycol(16)oleate, polyethylene glycol(17)oleate, polyethylene glycol(18) oleate, polyethylene glycol(19)oleate, polyethylene glycol(20)oleate.

Sodium laureth-11 carboxylate may advantageously be used as the ethoxylated alkyl ether carboxylic acid or salt thereof.

Sodium laureth-1-4 sulfate may advantageously be used as alkyl ether sulfate.

Polyethylene glycol(30)cholesteryl ether may advantageously be used as ethoxylated cholesterol derivative. Polyethylene glycol(25)soyasterol has also proven beneficial.

The polyethylene glycol(60) evening primrose glycerides may advantageously be used as ethoxylated triglycerides.

It may also be advantageous to choose the polyethylene glycol glycerin fatty acid esters from polyethylene glycol (20)glyceryl laurate, polyethylene glycol(21)glyceryl laurate, polyethylene glycol(22)glyceryl laurate, polyethylene glycol(23)glyceryl laurate, polyethylene glycol(6)glyceryl caprate/caprinate, polyethylene glycol(20)glyceryl oleate, polyethylene glycol(20)glyceryl isostearate, polyethylene glycol(18)glyceryl oleate/cocoate.

It may likewise be favorable to choose the sorbitan esters from polyethylene glycol(20)sorbitan monolaurate, polyethylene glycol(20)sorbitan monostearate, polyethylene glycol (20)sorbitan monoisostearate, polyethylene glycol(20)sorbitan monopalmitate, polyethylene glycol(20)sorbitan monooleate.

Non-limiting examples of advantageous W/O emulsifiers which may be used include: fatty alcohols having from about 8 to about 30 carbon atoms, monoglycerol esters of saturated and/or unsaturated, branched and/or unbranched alkanecarboxylic acids having a chain length of from about 8 to about 24, in particular from about 12 to about 18 carbon atoms, diglycerol esters of saturated and/or unsaturated, branched and/or unbranched alkanecarboxylic acids having a chain length of from about 8 to about 24, in particular from about 12 to about 18 carbon atoms, monoglycerol ethers of saturated and/or unsaturated, branched and/or unbranched alcohols having a chain length of from about 8 to about 24, in particular from about 12 to about 18 carbon atoms, diglycerol ethers of saturated and/or unsaturated, branched and/or unbranched alcohols having a chain length of from about 8 to about 24, in particular from about 12 to about 18 carbon atoms, propylene glycol esters of saturated and/or unsaturated, branched and/or unbranched alkanecarboxylic acids having a chain length of from about 8 to about 24, in particular from about 12 to about 18 carbon atoms, and sorbitan esters of saturated and/or unsaturated, branched and/or unbranched alkanecarboxylic acids having a chain length of from about 8 to about 24, in particular from about 12 to about 18 carbon atoms.

Particularly advantageous W/O emulsifiers comprise glyceryl monostearate, glyceryl monoisostearate, glyceryl monomyristate, glyceryl monooleate, diglyceryl monostearate, diglyceryl monoisostearate, propylene glycol monostearate, propylene glycol monoisostearate, propylene glycol monocaprylate, propylene glycol monolaurate, sorbitan monoisostearate, sorbitan monolaurate, sorbitan monocaprylate, sorbitan monoisooleate, sucrose distearate, cetyl alcohol, stearyl alcohol, arachidyl alcohol, behenyl alcohol, isobehenyl alcohol, selachyl alcohol, chimyl alcohol, polyethylene glycol(2)stearyl ether (steareth-2), glyceryl monolaurate, glyceryl monocaprinate, glyceryl monocaprylate.

Preparations according to the invention may advantageously contain other preservatives in addition to phenoxyethanol. The concentrations of the individual preservatives can thus be reduced, which often has an advantageous influence on the skin tolerance of the preparation, or preservatives of different action profiles can be combined with one another, thus substantially improving the overall protection of the preparation.

Sorbic acid and salts thereof, esters of para-hydroxybenzoic acid (parabens), advantageously the methyl, ethyl, propyl, butyl and isobutyl esters of parahydroxybenzoic acid, particularly advantageously mixtures of these esters, dibromhexamidine-2-bromo-2-nitro-1,3-propanediol, imidazolidinyl urea, polyaminopropyl biguanide, 1,3-bis-(hydroxymethyl)-5,5-dimethyl-2,4-imidazolidinedione (DMDM hydantoin), methylchloroisothiazolinone, methylisothiazolinone, diazolidinyl urea, benzoic acid, benzyl alcohol, iodopropynylbutyl carbamate and mixtures of these compounds, may advantageously be used in combination with phenoxyethanol for the improved protection of the preparation according to the invention.

DETAILED DESCRIPTION OF THE PRESENT INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description making apparent to those skilled in the art how the several forms of the present invention may be embodied in practice. Unless stated otherwise, all amounts, fractions and percentages given are based on the weight and the total amount or on the total weight of the preparations.

| Example 1 O/W emulsion | % by weight |
|---|---|
| Glyceryl stearate citrate | 2 |
| Shea butter | 2 |
| Stearyl alcohol | 2 |
| Cetyl alcohol | 3 |
| Hydrogenated coco glycerides | 2 |
| Caprylic acid/capric acid triglyceride | 1 |
| Ethylhexyl coco fatty acid ester | 2 |
| Cyclomethicone | 3 |
| Dicaprylyl ether | 3 |
| Tocopheryl acetate | 1 |
| Sodium ascorbyl phosphate | 0.1 |
| Panthenol | 1 |
| Ubiquinone (Q10) | 0.03 |
| Retinyl palmitate | 0.1 |
| Creatinine | 0.08 |
| Creatine | 1.0 |
| Phenoxyethanol | 0.8 |
| p-Hydroxybenzoic acid alkyl ester (paraben) | 0.6 |
| Ethylhexyl glycerin | 1 |
| Polyacrylic acid (carbomer) | 0.1 |
| Starch | 0.5 |
| Glycerin | 10 |
| Water-soluble and/or oil-soluble dyes | 0.05 |
| Fillers/additives (SiO$_2$, BHT, EDTA) | 0.2 |
| Perfume | q.s. |
| Water | ad 100 |

| Example 2 O/W emulsion | % by weight |
|---|---|
| Glyceryl stearate, self-emulsifying | 5 |
| Stearyl alcohol | 1 |
| Shea butter | 1 |
| $C_{12-15}$ Alkylbenzoate | 3 |
| Caprylic acid/capric acid triglyceride | 1 |
| Mineral oil | 1 |
| Dicaprylyl carbonate | 3 |
| Ethylhexyl cyanodiphenylacrylate (octocrylene) | 5 |
| Ethylhexyl triazone | 1 |
| Bis-ethylhexyloxyphenol methoxyphenyl triazine | 1 |
| Citric acid, sodium salt | 0.1 |
| Creatine | 0.1 |
| Phenoxyethanol | 0.6 |
| p-Hydroxybenzoic acid alkyl ester (paraben) | 0.3 |
| Hexamidine diisethionate | 0.04 |
| 1,3-Dimethylol-5,5-dimethylhydantoin (DMDM hydantoin) | 0.1 |
| Ethanol (denaturated) | 2 |
| Ammonium acryloyldimethyltaurate/vinyl pyrrolidone copolymers | 0.5 |
| Glycerin | 10 |
| Butylene glycol | 1 |
| Additives (distarch phosphate, SiO$_2$, BHT) | 1 |
| Perfume | q.s. |
| Water | ad 100 |

| Example 3 O/W emulsion | % by weight |
|---|---|
| Glyceryl stearate | 3 |
| PEG-40-stearate | 1 |
| Cetearyl alcohol | 2 |
| Shea butter | 2 |
| $C_{12-15}$ Alkyl benzoate | 2 |
| Coco glycerides | 2 |
| Octyldodecanol | 1 |
| Cyclomethicone | 4 |
| Beeswax | 1 |
| Ethylhexyl methoxycinnamate | 5 |
| Phenylbenzimidazole sulfonic acid | 2 |
| 2-Hydroxy 4-methoxy benzophenone (oxybenzone) | 3 |

| Example 3 O/W emulsion | % by weight |
|---|---|
| Ubiquinone (Q10) | 0.03 |
| Sodium ascorbylphosphate | 0.1 |
| Tocopheryl acetate | 1 |
| Creatine | 0.5 |
| Methylpropanediol, | 1 |
| Phenoxyethanol | 0.3 |
| p-Hydroxybenzoic acid alkyl ester (paraben) | 0.2 |
| Diazolidinyl urea | 0.1 |
| Carbomer | 0.1 |
| Carrageenan | 0.1 |
| Glycerin | 7 |
| Additives (starch phosphate, BHT) | 2 |
| Perfume | q.s. |
| Water | ad 100 |

| Example 4 O/W emulsion | % by weight |
|---|---|
| Glyceryl stearate | 1 |
| Stearic acid | 3 |
| Stearyl alcohol | 3 |
| Cetyl alcohol | 2 |
| $C_{12-15}$ Alkyl benzoate | 2 |
| Caprylic acid/capric acid triglyceride | 2 |
| Macademia oil | 1 |
| Shea butter | 2 |
| Beeswax | 1 |
| Dimethicones | 1 |
| Hydrogenated coco glycerides | 1 |
| Ethylhexyl glycerin | 0.5 |
| Tocopheryl acetate | 1 |
| Creatinine | 0.1 |
| Creatine | 0.8 |
| Ubiquinone (Q10) | 0.03 |
| Retinyl palmitate | 0.1 |
| Phenoxyethanol | 0.2 |
| p-Hydroxybenzoic acid alkyl ester (paraben) | 0.3 |
| Iodopropynyl butylcarbamate | 0.02 |
| Cyclodextrin | 0.5 |
| Iminodisuccinate | 0.2 |
| Carbomer | 0.3 |
| Glycerin | 5 |
| Butylene glycol | 1 |
| Methylpropanediol | 1 |
| Additives ($SiO_2$, BHT, talc) | 0.5 |
| Perfume | q.s. |
| Water | ad 100 |

| Example 5 O/W emulsion | % by weight |
|---|---|
| Glyceryl stearate | 2 |
| PEG-40-stearate | 1 |
| Myristyl myristate | 1 |
| Cetearyl alcohol | 2 |
| Shea butter | 2 |
| $C_{12-15}$ Alkyl benzoate | 3 |
| Caprylic acid/capric acid triglyceride | 2 |
| Ethylhexyl coco fatty acid ester | 1 |
| Vaseline | 2 |
| Cyclomethicone | 5 |
| $TiO_2$ | 1 |
| Ethylhexyl methoxycinnamate | 3 |
| 2-Hydroxy 4-methoxy benzophenone (oxybenzone) | 2 |
| Ubiquinone (Q10) | 0.05 |
| Tocopheryl acetate | 0.5 |
| Creatinine | 0.2 |
| Creatine | 1.0 |
| Retinyl palmitate | 0.1 |
| Sodium ascorbyl phosphate | 0.1 |
| Phenoxyethanol | 0.2 |
| p-Hydroxybenzoic acid alkyl ester (paraben) | 0.3 |
| Polyacrylic acid (carbomer) | 0.1 |
| Aluminum starch octenylsuccinate | 0.5 |
| Glycerin | 5 |
| Fillers/additives (distarch phosphate, $SiO_2$, BHT, talc, aluminum stearate) | 0.05 |
| Perfume | q.s |
| Water | ad 100 |

| Example 6 O/W emulsion | % by weight |
|---|---|
| Cetyl alcohol | 2 |
| Shea butter | 1 |
| Caprylic acid/capric acid triglyceride | 2 |
| Octyldodecanol | 1 |
| Dicaprylyl carbonate | 5 |
| Dimethylpolysiloxane (dimethicone) | 1 |
| Polydecene | 2 |
| Creatine | 1 |
| Ethylhexyl methoxycinnamate | 3 |
| Bis-ethylhexyloxyphenol methoxyphenyl triazine | 0.5 |
| Sodium ascorbyl phosphate | 0.05 |
| Iminodisuccinate | 0.2 |
| Ubiquinone | 0.05 |
| Phenoxyethanol | 0.3 |
| p-Hydroxybenzoic acid alkyl ester | 0.4 |
| Alkylacrylate crosspolymer | 0.2 |
| Glycerin | 5 |
| Perfume | q.s. |
| Water | ad 100 |

| Example 7 O/W emulsion | % by weight |
|---|---|
| Glyceryl stearate | 2.5 |
| PEG-40-stearate | 1 |
| Cetearyl alcohol | 2 |
| Hydrogenated coco glycerides | 1 |
| Shea butter | 2 |
| $C_{12-15}$ alkyl benzoate | 4 |
| Caprylic acid/capric acid triglyceride | 2 |
| Octyldodecanol | 1 |
| Vaseline | 1 |
| Dicaprylyl carbonate | 3 |
| $TiO_2$ | 1 |
| Ethylhexyl cyanodiphenylacrylate (octocrylene) | 5 |
| Phenylbenzimidazole sulfonic acid | 1 |
| 2-Hydroxy 4-methoxy benzophenone (oxybenzone) | 2 |
| Ubiquinone (Q10) | 0.03 |
| Creatinine | 0.02 |
| Creatine | 0.05 |
| Cyclodextrin | 0.2 |
| Iminodisuccinate | 0.2 |
| Phenoxyethanol | 0.5 |
| p-Hydroxybenzoic acid alkyl ester (paraben) | 0.4 |
| Iodopropynyl butylcarbamate | 0.05 |
| 2-ethylhexylglycerin ether (octoxyglycerin) | 0.5 |
| Polyacrylic acid (carbomer) | 0.2 |
| Nylon microparticle | 1 |
| Glycerin | 10 |
| Additives (distarch phosphate, $SiO_2$, talc, BHT, aluminum stearate) | 0.03 |
| Perfume | q.s. |
| Water | ad 100 |
| Polyglyceryl-3-methylglucose-distearate | 2 |
| Cetyl alcohol | 1 |
| $C_{12-15}$ Alkyl benzoate | 2 |
| Butyleneglycol dicaprylate/dicaprate | 2 |
| Caprylic acid/capric acid triglyceride | 2 |
| Hydrogenated polydecene | 1 |

| Example 7 O/W emulsion | % by weight |
|---|---|
| Dimethylpolysiloxane (dimethicone) | 1 |
| Isodecyl neopentanoate | 4 |
| Creatinine | 0.1 |
| Creatine | 1 |
| Sodium ascorbyl phosphate | 0.1 |
| EDTA | 0.2 |
| Phenoxyethanol | 0.4 |
| Iodopropynyl butylcarbamate | 0.05 |
| p-ydroxybenzoic acid alkyl ester (paraben) | 0.4 |
| Ethanol denatured | 2 |
| Carbomer | 0.2 |
| Iminodisuccinate | 0.2 |
| Glycerin | 5 |
| Additives (distarch phosphate, talc, BHT) | 0.2 |
| Perfume | q.s. |
| Water | ad 100 |

| Example 8 O/W emulsion | % by weight |
|---|---|
| Polyglyceryl-3-methylglucose distearate | 2 |
| Sorbitan stearate | 1 |
| Behenyl alcohol | 2 |
| Cetyl alcohol | 1 |
| $C_{12-15}$ Alkyl benzoate | 2 |
| Butyleneglycol dicaprylate/dicaprate | 2 |
| Caprylic acid/capric acid triglyceride | 2 |
| Hydrogenated polydecene | 1 |
| Dimethylpolysiloxane (dimethicone) | 1 |
| Dicaprylyl carbonate | 2 |
| Ethylhexyl methoxycinnamate | 5 |
| Butyl methoxydibenzoylmethane | 2 |
| Creatine | 0.1 |
| Tocopheryl acetate | 0.5 |
| Iminodisuccinate | 0.2 |
| Phenoxyethanol | 0.4 |
| p-Hydroxybenzoic acid alkyl ester (paraben) | 0.4 |
| Ethanol denatured | 5 |
| Xanthan gum | 0.2 |
| Ammonium acryloyldimethyltaurate/ vinylpyrrolidone copolymer | 0.3 |
| Glycerin | 4.5 |
| Additives (distarch phosphate, $SiO_2$, EDTA, BHT) | 0.5 |
| Perfume | q.s. |
| Water | ad 100 |

| Example 9 O/W emulsion | % by weight |
|---|---|
| Cetearyl glucoside | 2 |
| Myristyl myristate | 1 |
| Stearyl alcohol | 4 |
| $C_{12-15}$ Alkyl benzoate | 2 |
| Caprylic acid/capric acid triglyceride | 3 |
| Hydrogenated polydecene | 1 |
| Dicaprylyl carbonate | 3 |
| Polydecene | 4 |
| Ethylhexyl methoxycinnamate | 3 |
| Ethylhexyl cyanodiphenylacrylate (octocrylene) | 3 |
| Butyl methoxydibenzoylmethane | 1 |
| Creatine | 1.5 |
| Ubiquinone (Q10) | 0.1 |
| Tocopheryl acetate | 1 |
| Trisodium EDTA | 0.1 |
| Phenoxyethanol | 0.7 |
| p-Hydroxybenzoic acid alkyl ester (paraben) | 0.4 |
| Ethylhexyl glycerin | 0.4 |
| Ammonium polyacryloyldimethyl taurate | 0.3 |
| Aluminum starch octenylsuccinate | 1 |
| Glycerin | 4 |
| Butyleneglycol | 2 |
| Additives (talc, BHT, dye) | 1 |
| Perfume | q.s. |
| Water | ad 100 |

| Example 10 O/W emulsion | % by weight |
|---|---|
| Glyceryl stearate | 1 |
| Stearic acid | 2.5 |
| Behenyl alcohol | 2 |
| Cetyl alcohol | 3 |
| Hydrogenated coco glycerides | 1 |
| $C_{12-15}$ Alkyl benzoate | 2 |
| Octyldodecanol | 2 |
| Octamethyltetrasiloxane (cyclomethicone) | 2 |
| Dimethylpolysiloxane (dimethicone) | 1 |
| Dicaprylylcarbonate | 4 |
| $TiO_2$ | 1 |
| Ethylhexyl methoxycinnamate | 2 |
| Ubiquinone (Q10) | 0.05 |
| Creatine | 0.1 |
| Cyclodextrin | 0.3 |
| Tocopheryl acetate | 0.5 |
| Iminodisuccinate | 0.1 |
| Phenoxyethanol | 0.3 |
| p-Hydroxybenzoic acid alkyl ester (paraben) | 0.6 |
| Ethanol denatured | 3 |
| Polyacrylic acid (carbomer) | 0.2 |
| Glycerin | 7 |
| Additives (distarch phosphate, $SiO_2$, talc, BHT, aluminum stearate) | 1 |
| Perfume | q.s. |
| Water | ad 100 |

| Example 11 O/W emulsion | 11 |
|---|---|
| Polyethylene glycol(21) stearyl ether (steareth 21) | 2 |
| Polyethylene glycol(2) stearyl ether (steareth 2) | 1 |
| Cetearyl alcohol | 2 |
| Shea butter | 1 |
| $C_{12-15}$ Alkyl benzoate | 2 |
| Octyldodecanol | 1 |
| Mineral oil | 3 |
| Octamethyltetrasiloxane (cyclomethicone) | 4 |
| Dicaprylylether | 2 |
| $TiO_2$ | 1 |
| Ethylhexyl methoxycinnamate | 4 |
| Ethylhexyltriazone | 1 |
| Ubiquinone (Q10) | 0.02 |
| Creatinine | 0.12 |
| Creatine | 1.0 |
| Biotin | 0.02 |
| Trisodium EDTA | 0.2 |
| Phenoxyethanol | 0.5 |
| p-Hydroxybenzoic acid alkyl ester (paraben) | 0.3 |
| Iodopropynyl butylcarbamate | 0.1 |
| Polyacrylic acid (carbomer) | 0.2 |
| Ammonium acryloyldimethyltaurate/vinylpyrrolidone copolymers | 0.3 |
| Glycerin | 6 |
| Additives (distarch phosphate, $SiO_2$, talc, BHT, aluminum stearate) | 0.05 |
| Perfume | q.s. |
| Water | ad 100 |

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A cosmetic or dermatological O/W emulsion which comprises
   (I) at least one of creatine and a creatine derivative selected from creatine phosphate, creatine sulfate, creatine acetate, creatine ascorbate, and an ester of creatine and a mono- or polyfunctional alcohol;
   (II) phenoxyethanol;
   (III) at least one of (i) creatinine and (ii) glycerin;
   wherein the emulsion further comprises carnitine and/or a derivative thereof.

2. The emulsion of claim 1, wherein the emulsion comprises from about 0.01% to about 1% by weight of (I).

3. The emulsion of claim 2, wherein the emulsion comprises from about 0.1% to about 1% by weight of (II).

4. The emulsion of claim 1, wherein the emulsion comprises
   (I) from about 0.1% to about 1% by weight of at least one of creatine and creatine phosphate;
   (II) from about 0.1% to about 1% by weight of phenoxyethanol;
   (III) at least one of (i) from about 0.1% to about 1% by weight of creatinine and (ii) from about 4% to about 15% by weight of glycerin.

5. The emulsion of claim 4, wherein both (III)(i) and (III)(ii) are present.

6. The emulsion of claim 4, wherein no (III)(i) is present.

7. The emulsion of claim 1, wherein the emulsion has a pH of from about 6.5 to about 8.0.

8. The emulsion of claim 1, wherein the emulsion comprises at least 0.2% by weight of phenoxyethanol.

9. The emulsion of claim 1, wherein the emulsion further comprises at least one of a UVA filter and a UVB filter.

10. The emulsion of claim 1, wherein the emulsion further comprises ubiquinone.

11. The emulsion of claim 9, wherein the emulsion further comprises ubiquinone.

12. The emulsion of claim 10, wherein the emulsion further comprises retinyl palmitate.

13. The emulsion of claim 1, wherein the emulsion further comprises panthenol.

14. The emulsion of claim 1, wherein the emulsion further comprises at least one of evening primrose oil and macadamia nut oil.

15. The emulsion of claim 1, wherein the emulsion further comprises one or more ceramides.

* * * * *